(12) United States Patent
Neumann

(10) Patent No.: US 11,984,226 B2
(45) Date of Patent: *May 14, 2024

(54) SYSTEMS AND METHODS FOR SELECTING AN INTERVENTION BASED ON EFFECTIVE AGE

(71) Applicant: KPN INNOVATIONS, LLC., Lakewood, CO (US)

(72) Inventor: Kenneth Neumann, Lakewood, CO (US)

( * ) Notice: Subject to any disclaimer, the term of this patent is extended or adjusted under 35 U.S.C. 154(b) by 192 days.

This patent is subject to a terminal disclaimer.

(21) Appl. No.: 17/541,606

(22) Filed: Dec. 3, 2021

(65) Prior Publication Data

US 2022/0093263 A1    Mar. 24, 2022

Related U.S. Application Data

(63) Continuation of application No. 16/558,502, filed on Sep. 3, 2019, now Pat. No. 11,227,691.

(51) Int. Cl.
*G16H 50/20* (2018.01)
*G01N 33/50* (2006.01)
(Continued)

(52) U.S. Cl.
CPC ......... *G16H 50/20* (2018.01); *G01N 33/5005* (2013.01); *G01N 33/74* (2013.01);
(Continued)

(58) Field of Classification Search
CPC ........ G16H 10/00; G16H 10/20; G16H 10/40; G16H 15/00; G16H 20/00; G16H 20/10;
(Continued)

(56) References Cited

U.S. PATENT DOCUMENTS

2007/0179809 A1 *   8/2007   Brown .................... G16H 20/00
                                                                600/300
2013/0171630 A1 *   7/2013   Qin ....................... C12Q 1/6876
                                                                435/6.11
(Continued)

OTHER PUBLICATIONS

Caballero et al. 2017, "Advanced analytical methodologies for measuring healthy ageing and its determinants, using factor analysis and machine learning techniques: the ATHLOS project," Sci Rep. Mar. 10, 2017;7:43955. doi: 10.1038/srep43955. PMID: 28281663; PMCID: PMC5345043.*

(Continued)

*Primary Examiner* — Robert W Morgan
*Assistant Examiner* — Charles P Coleman
(74) *Attorney, Agent, or Firm* — Caldwell Intellectual Property Law

(57) ABSTRACT

System for selecting an intervention based on effective age, system including at least a server designed and configured to obtain user data from a user database. The server further configured to project an actuarial life expectancy using a user chronological age. The server further configured to calculate a variance between the actuarial life expectancy and a projected actual mortality date, including receiving training data correlating an aspect of the user data to the variance, generating a machine learning model that receives one or more aspects of the user data as inputs and produces an output of the variance, and determining the variance using the machine learning model. The server further configured to generate a plurality of interventions including an intervention vector, wherein each intervention vector entry indicates a degree of impact. The server further configured to select an intervention as a function of the degrees of impact and the variance.

20 Claims, 6 Drawing Sheets

(51) Int. Cl.
　　　*G01N 33/74* (2006.01)
　　　*G06F 17/18* (2006.01)
　　　*G06F 18/2413* (2023.01)
　　　*G06N 20/10* (2019.01)
　　　*G16H 50/30* (2018.01)

(52) U.S. Cl.
　　　CPC ........ *G06F 17/18* (2013.01); *G06F 18/24147* (2023.01); *G06N 20/10* (2019.01); *G16H 50/30* (2018.01)

(58) Field of Classification Search
　　　CPC ........ G16H 20/13; G16H 20/17; G16H 30/00; G16H 40/00; G16H 50/00; G16H 70/00; G16H 80/00; G16H 50/20; G16H 50/30; G06Q 50/22–24; G06N 20/10; G06F 18/24147; G06F 17/18; G01N 33/5005; G01N 33/74

USPC .................................................. 705/2, 3, 20
See application file for complete search history.

(56) References Cited

U.S. PATENT DOCUMENTS

| | | | |
|---|---|---|---|
| 2016/0180050 A1* | 6/2016 | Holmes | G16H 10/65 |
| | | | 705/3 |
| 2016/0232313 A1* | 8/2016 | Apte | G16B 50/10 |
| 2019/0272890 A1* | 9/2019 | Aliper | A61K 35/28 |

OTHER PUBLICATIONS

Pyrkov et al. 2018, "Extracting biological age from biomedical data via deep learning: too much of a good thing?," Sci Rep. Mar. 26, 2018;8(1):5210. doi: 10.1038/s41598-018-23534-9. PMID: 29581467; PMCID: PMC5980076.*

* cited by examiner

SYSTEMS AND METHODS FOR SELECTING AN INTERVENTION BASED ON EFFECTIVE AGE

CROSS-REFERENCE TO RELATED APPLICATIONS

This application is a continuation of Non-provisional application Ser. No. 16/558,502 filed on Sep. 3, 2019, and entitled "SYSTEMS AND METHODS FOR SELECTING AN INTERVENTION BASED ON EFFECTIVE AGE," the entirety of which is incorporated herein by reference.

FIELD OF THE INVENTION

The present invention generally relates to the field of artificial intelligence. In particular, the present invention is directed to systems and methods for selecting an intervention based on effective age.

BACKGROUND

Analysis and recommendation generation regarding longevity is currently fraught with imprecision, due to the multiplicity of factors involved. This is further complicated by a lack of quantitative measures indicative of implementation of solutions; statistical soundness of a model is only predictive inasmuch as it reflects genuine feasibility of aggregated outputs.

SUMMARY OF THE DISCLOSURE

In an aspect, a system for selecting an intervention based on effective age, the system including at least a server, the at least a server designed and configured to obtain user data from a user database, wherein the user data includes data corresponding to user tests and a user chronological age. The server further configured to project an actuarial life expectancy using the user chronological age. The server further configured to calculate a variance between the actuarial life expectancy and a projected actual mortality date, wherein calculating the variance includes receiving training data, wherein the training data correlates an aspect of the user data to the variance between the actuarial life expectancy and a projected actual mortality date, generating, using a supervised machine learning process, a machine learning model that receives one or more aspects of the user data as inputs and produces an output of the variance between the actuarial life expectancy and a projected actual mortality date, and determining the variance between the actuarial life expectancy and a projected actual mortality date using the machine learning model. The server further configured to generate a plurality of interventions, wherein each intervention of the plurality of interventions includes an intervention vector having a plurality of intervention vector entries, wherein each intervention vector entry indicates a degree of impact. The server further configured to select an intervention from the plurality of interventions as a function of the degrees of impact and the variance between the actuarial life expectancy and a projected actual mortality date.

In another aspect, a method for selecting an intervention based on effective age, the method including obtaining user data from a user database, wherein the user data includes data corresponding to user tests and a user chronological age. The method further including projecting an actuarial life expectancy using the user chronological age. The method further including calculating a variance between the actuarial life expectancy and a projected actual mortality date, wherein calculating the variance includes receiving training data, wherein the training data correlates an aspect of the user data to the variance between the actuarial life expectancy and a projected actual mortality date, generating, using a supervised machine learning process, a machine learning model that receives one or more aspects of the user data as inputs and produces an output of the variance between the actuarial life expectancy and a projected actual mortality date, and determining the variance between the actuarial life expectancy and a projected actual mortality date using the machine learning model. The method further including generating a plurality of interventions, wherein each intervention of the plurality of interventions includes an intervention vector having a plurality of intervention vector entries, wherein each intervention vector entry indicates a degree of impact. The method further including selecting an intervention from the plurality of interventions as a function of the degrees of impact and the variance between the actuarial life expectancy and a projected actual mortality date.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Embodiments disclosed herein use a combination of machine learning processes to determine an effective age of a person based on physically extracted samples. A vector weighting various objectives as derived by further processes is used to match one or more potential interventions for improvement of effective age by minimizing a loss function to find a best-match solution. Classification of data to endocrinal life phases may be used to limit training data to closely matched cohorts.

Figure 1:
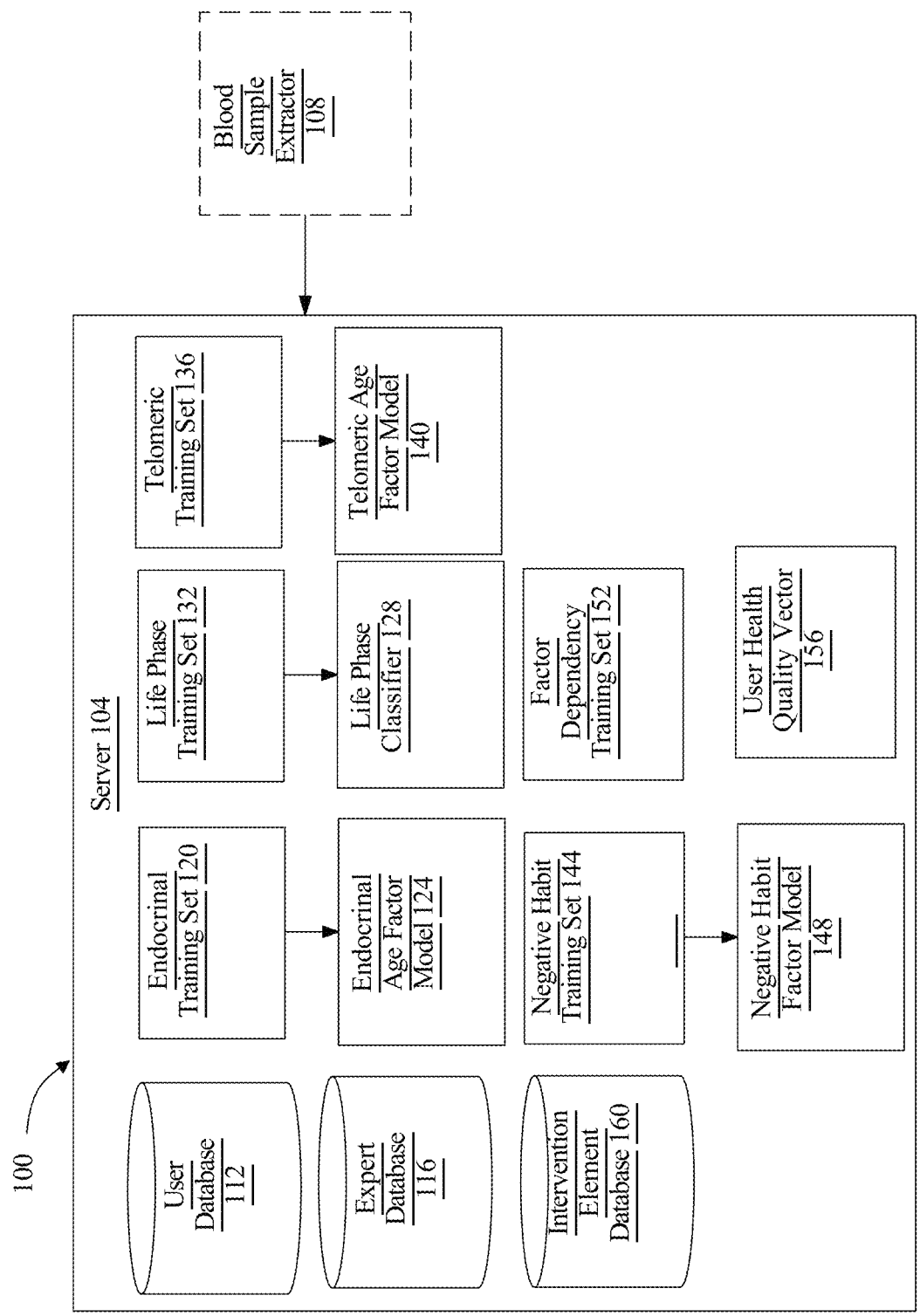
FIG. 1 is a block diagram illustrating an exemplary embodiment of a system for selecting an intervention based on effective age.

Referring now to FIG. 1, an exemplary embodiment of a system 100 for selecting an intervention based on effective age is illustrated. System 100 includes at least a server 104. At least a server 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. At least a server 104 may include a single computing device operating independently, or may include two or more computing device operating in concert, in parallel, sequentially or the like; two or more computing devices may be included together in a single computing device or in two or more computing devices. At least a server 104 may interact with one or more additional devices as described below in further detail via a network interface device. Network interface device may be utilized for connecting at least a server 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. At least a server 104 may include but is not limited to, for example, a computing device or cluster of computing devices in a first location and a second computing device or cluster of computing devices in a second location. At least a server 104 may include one or more computing devices dedicated to data storage, security, distribution of traffic for load balancing, and the like. At least a server 104 may distribute one or more computing tasks as described below across a plurality of computing devices of computing device, which may operate in parallel, in series, redundantly, or in any other manner used for distribution of tasks or memory between computing devices. At least a server 104 may be implemented using a "shared nothing" architecture in which data is cached at the worker, in an embodiment, this may enable scalability of system 100 and/or computing device.

With continued reference to FIG. 1, at least a server 104 may be designed and/or configured to perform any method, method step, or sequence of method steps in any embodiment described in this disclosure, in any order and with any degree of repetition. For instance, at least a server 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. At least a server 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, at least a server 104 may be configured to record a user blood test indicating at least a measure of user endocrine function. Recording a user blood test, as used herein, may include receiving or extracting data from a user blood test. User blood test may be extracted and/or analyzed by a blood sample extractor 108, which may be integrated in at least a server 104, connected to at least a server 104, in communication with at least a server 104, and/or may operate independently of at least a server 104; data acquired and/or extracted by blood sample extractor 108 may be transmitted or otherwise provided to at least a server 104 using any suitable process for transfer of electronic data and/or memory. As a further non-limiting example, a person may enter data into a device connected to and/or communicating with at least a server 104, describing one or more user blood test elements and/or results; person may be a medical professional, defined for the purposes of this disclosure as a person that performs any phase of medical diagnosis and/or treatment, including without limitation a doctor, nurse, medical technician, diagnostic test technician, lab technician, or the like.

Continuing to refer to FIG. 1, user blood test indicates at least a measure of endocrine function, where "at least a measure of endocrine function," as used in this disclosure, is at least a diagnostic datum indicating a state of health of a user's endocrine system. At least a measure of endocrine function may include at least an endocrine level, where an "endocrine level" is defined as an amount of a hormone as detected in a blood sample. An endocrine level may include, without limitation, a level of estrogen, testosterone, human growth hormone, melatonin, aldosterone, calcitonin, renin, prolactin, follicle-stimulating hormone, luteinizing hormone, norepinephrine, epinephrine, parathyroid hormone, cortisol, insulin, thyroid hormones, cholesterol, dehydroepiandrosterone (DHEAS), DHEA-Sulfate, insulin-like growth factor 1 (IGF-1), adipokines such as adiponectin, leptin, and/or ghrelin, somatostatin, gonadotropin-releasing hormone (GnRH) and/or progesterone, as well as ratios and/or relative quantities of endocrine levels, such as without limitation a ratio of DHEAS to cortisol. Measures of endocrinal function may include a change in at least an endocrinal level; for instance, user may have started with a given level of a hormone or other endocrinal chemical, which may have been determined using a previous blood sample, and which may have changed prior to the extraction of an instant blood sample. This may be recorded in any suitable data form, including as an absolute change, a relative change, a percentage, or the like.

Still referring to FIG. 1, recording user blood test may include recording and/or receiving additional data that may be extracted from blood tests, including without limitation toxicology data, including data indicative of chemical contamination, levels of chemicals consistent with drug use, or the like. Additional data may include data indicative of damage to one or more organs such as without limitation liver damage, kidney damage, or the like. Additional blood sample data may include hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Additional blood sample data may include data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Additional blood sample data may include data of glucose metabolism such as fasting glucose levels and/or hemoglobin A1-C (HbA1c) levels. Additional blood sample data may include may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline photophatase, alanine amino transferase, aspartate amino transferase, lactate dehydrogenase (LDH), bilirubin, gamma-glutamyl transferase (GGT), iron, and/or total iron binding capacity (TIBC), or the like.

Still referring to FIG. 1, at least a measure of user endocrine function may be stored in a user database 112. User database 112 may include any data structure for ordered storage and retrieval of data, which may be implemented as a hardware or software module. A user database 112 may be implemented, without limitation, as a relational database, a key-value retrieval datastore such as a NOSQL database, or any other format or structure for use as a datastore that a person skilled in the art would recognize as suitable upon review of the entirety of this disclosure. A user database 112 may include a plurality of data entries and/or records corresponding to user tests as described above. Data entries in a user database 112 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a user database 112 may reflect categories, cohorts, and/or populations of data consistently with this disclosure.

With continued reference to FIG. 1, at least a server 104 is configured to determine a user endocrinal age factor using the at least a measure of user endocrine function. A "user endocrinal age factor," as used in this disclosure, is a factor that may be multiplied by a user's chronological age to reflect an effect that endocrinal data has on the user's effective age. A user's "chronological age," as defined in this disclosure, is an age of the user as measured in years, or other units of time, from the date of the user's birth to the date of the measurement, where a "date" may include any calendar date, Julian date, or the like. A chronological age may be used to project a user's "actuarial life expectancy," defined as a probable age of death, as predicted using any actuarial method and/or table, and/or an interval from a date such as the present date to the probable age of death; actuarial methods may include looking up and/or calculating a user's life expectancy using date of birth and/or demographic information about the user such as sex, ethnicity, geographic location, nationality, or the like. A "user effective age," as used in this disclosure, is an age of a user as adjusted to reflect a life expectancy that differs from an actuarially projected life expectancy. For instance, a user effective age of a person predicted to life fewer years than actuarially projected may be higher than a user effective age of a person predicted to match and/or exceed an actuarially projected life expectancy. User effective age may be used as a representation of a user's likely overall state of health, inasmuch as a user's likelihood to exceed or fall short of actuarially projected life expectancy may be closely linked to a user's state of health.

Still referring to FIG. 1, calculation may include prediction of a variance from actuarial life expectancy for a given person, where a "variance from actuarial life expectancy" is a difference between an actuarial life expectancy for that person and a projected number of years until death as determined based on the at least a measure of user endocrine function. A difference between these two values may be added to a user chronological age and then divided by the user chronological age to calculate a "raw" factor, which may represent an estimated effect of endocrinal measures on life expectancy without regard for relatedness to other variables; a raw factor may then be multiplied by a weight to determine the endocrinal age factor, where the weight may account for interrelatedness between endocrinal measures and other measures used to calculate user effective age as described herein. Processes for determination and/or calculation of weights for this purpose may be performed as described in further detail below.

With continued reference to FIG. 1, at least a server 104 may determine a user endocrinal age factor using one or more endocrine levels and/or changes in endocrine levels as described above. For instance, and without limitation, a preadolescent child may experience increase and/or decreases in growth hormone which may be consistent with different stages in childhood development and growth. As a further non-limiting example, various stages of adolescence may similarly be associated with increases in GnRH, luteinizing hormone, follicle-stimulating hormone, testosterone (which may particularly increase in boys), and/or estrogen (which may particularly increase in girls). As an additional non-limiting example, various points and/or phases of an aging process may be associated with decreases in hormones such as without limitation decreases in estrogen, for instance in women, decreases in testosterone, for instance in men, decreases in growth hormone, decreases in melatonin, decreases in aldosterone, deceases in calcitonin, decreases in renin, and/or decreases in prolactin. As a further non-limiting example, various points and/or phases of an aging process may be associated with increases in hormones, such as without limitation increases in follicle-stimulating hormone, increases in luteinizing hormone, increases in norepinephrine, increases in parathyroid hormone, and/or increases in epinephrine, for instance in persons with extremely advanced age.

Continuing to refer to FIG. 1, at least a server 104 may determine user endocrinal age factor by retrieving user endocrinal age factor from an expert database 116. Expert database 116 may be implemented in any way suitable for implementation of user database 112 as described above. Expert submissions may be provided in any suitable manner, including using one or more entries on a user interface provided on an expert client device or the like, for instance according to embodiments as described in further detail below.

Alternatively or additionally, and still referring to FIG. 1, at least a server 104 may determine a user endocrinal age factor using one or more machine-learning and/or deep learning processes. A machine learning process is a process that automatedly uses a body of data known as "training data" and/or a "training set" to generate an algorithm that will be performed by a computing device/module to produce outputs given data provided as inputs; this is in contrast to a non-machine learning software program where the commands to be executed are determined in advance by a user and written in a programming language.

With continued reference to FIG. 1, at least a server 104 may perform machine learning tasks as described herein using regression algorithms and/or models, including without limitation linear regression algorithms and/or models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Still referring to FIG. 1, machine-learning algorithms used and/or implemented by at least a server 104 may include, without limitation, linear discriminant analysis. Machine-learning algorithms may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest-neighbors algorithms including without limitation K-nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

With continued reference to FIG. 1, machine-learning algorithms may include supervised machine-learning algorithms. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include sensor data and/or data produced via analysis as described above as inputs, degrees of risk and/or degrees of driver inattentiveness as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine learning algorithms that may be used to determine relation between inputs and outputs.

Still referring to FIG. 1, supervised machine-learning processes may include classification algorithms, defined as processes whereby a computing device derives, from training data, a model for sorting inputs into categories or bins of data. Classification may be performed using, without limitation, linear classifiers such as without limitation logistic regression and/or naive Bayes classifiers, nearest neighbor classifiers, support vector machines, decision trees, boosted trees, random forest classifiers, and/or neural network-based classifiers.

With continued reference to FIG. 1, machine learning processes may include unsupervised processes. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 1, machine-learning processes as described in this disclosure may be used to generate machine-learning models. A machine-learning model, as used herein, is a mathematical representation of a relationship between inputs and outputs, as generated using any machine-learning process including without limitation any process as described above, and stored in memory; an input is submitted to a machine-learning model once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning, for instance for multi-layered networks.

Alternatively or additionally, and still referring to FIG. 1, machine-learning may be performed without creating models, for instance via a lazy-learning process. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data. Heuristic may include selecting some number of highest-ranking associations and/or training data elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

With continued reference to FIG. 1, training data, as used herein, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by at least a server 104 may correlate any input data as described in this disclosure to any output data as described in this disclosure.

Continuing to refer to FIG. 1, and as a non-limiting illustrative example, at least a server 104 may determine endocrinal age factor by receiving an endocrinal training set 120 correlating at least a measure of user endocrine function and/or a change in at least a measure of user endocrine function to variances between actuarial life expectancy data and actual mortality dates. An "actuarial life expectancy datum," as used herein, is a datum indicating an age of death of a subject person, as predicted by reference to actuarial calculations and/or tables, for instance as described above; indication may be achieved, without limitation, using a datum containing actuarial life expectancy and/or a datum that may be used to determine actuarial life expectancy. An "actual mortality date" as used herein, is a date on which a person actually died; elements or entries in training data may include data concerning people who have died, enabling actual mortality date to be determined. An actual mortality date may include a measure of time between the date of a given measurement and the death of the person with regard to whom the measurement was taken, which may be represented as a calendar date and/or as a number of years after the date of measurement. A "variance between actuarial life expectancy datum and actual mortality date" may include a difference between a life expectancy as determined by actuarial life expectancy and actual mortality date, which may be determined by any suitable measure of difference between numerical quantities, including without limitation by subtraction. "Correlation" in a training data set may include any relation established therein linking one datum to another, including inclusion together in a data element, row, column, cell, or the like, and/or by giving each a common indicator and/or label indicative of their correlation in data used to create and/or compile training data. Correlation of at least a measure of user endocrine function and/or a change in at least a measure of user endocrine function to variances between actuarial life expectancy data and actual mortality dates may be accomplished by correlating to a calculated variance, to a factor based on the calculated variance, which may include an endocrinal age factor; alternatively or additionally, such correlation may indicate correlation to actuarial life expectancy datum and/or a dataset suitable for looking up actuarial life expectancy, and to actual mortality date, or any other set of data from which such a variance may be deduced. In other words, and by way of illustration only, an actual mortality date per se may not be in a training set entry; instead it might be a difference between actuarial and actual life expectancies, a life expectancy plus chronological age (from which variance may be calculated), or the like. Endocrinal training set 120 may include a plurality of entries, each entry correlating at least a measure of user endocrine function and/or a change in at least a measure of user endocrine function to a variance between actuarial life expectancy data and actual mortality date of a person.

Still referring to FIG. 1, at least a server 104 may perform one or more processes to modify and/or format training data to produce endocrinal training set 120. At least a server 104 may, without limitation, modify entries in training data to contain consistent forms of a variance, for instance so that a regression process or other supervised machine-learning process may operate without converting data to particular forms during operation; alternatively, supervised machine-learning process may perform standardization calculations during operation. Other modifications may include receiving a training set correlating one or more other biomarkers to variances between actuarial life expectancy data and actual mortality dates, where variances, correlations, and entries may be implemented as described above; for instance, training data relating endocrinal levels and/or changes in endocrinal levels to variances between actuarial life expectancy data and actual mortality dates may be unavailable, but a training set relating one or more additional biomarkers to variances between actuarial life expectancy data and actual mortality dates may be received. At least a server 104 may use one or more additional machine learning processes to create endocrinal training set 120 relating at least a measure of endocrine function to variances between actuarial life expectancy data and actual mortality dates by modifying training data relating one or more additional biomarkers to variances between actuarial life expectancy data and actual mortality dates. For instance, and without limitation, at least as server may perform an unsupervised machine learning process on training data correlating endocrinal measures with additional biomarkers, which may be any biomarkers; unsupervised machine learning may be used to cluster at least a measure of user endocrine function and/or a change in at least a measure of user endocrine function with one or more other biomarkers, for instance to identify one or more additional biomarkers that are highly correlated with endocrinal measures. At least a server 104 may then modify the training data to create endocrinal training set 120 by replacing one or more additional biomarkers in each entry the training data with at least a measure of endocrine function that is correlated therewith by the unsupervised machine learning set. In an embodiment, this approach may make it possible to draw upon training data relating one or more biomarkers to mortality to at least a measure of endocrine function; as data describing actual dates of death may require data collection over a number of years, whereas data relating an additional biomarker to at least a measure of endocrine function may be collected rapidly. In an embodiment, the one or more additional biomarkers may include a first measure of endocrine function, and the at least a measure of endocrine function may include a second measure of endocrine function, enabling replacement of a first measure of endocrine function with a second measure of endocrine function in first endocrine training set. In another embodiment, one or more additional biomarkers does not include any measure of endocrine function; for instance, one or more additional biomarkers may include a measure of cardiac function, mobility, body fat percentage, or the like.

With continued reference to FIG. 1, where endocrinal training set 120 correlates at least a measure of user endocrine function to variances between actuarial life expectancy and actual mortality dates, at least a server 104 may use the endocrinal training set 120 to generate an endocrinal age factor model 124, which may include any machine-learning model that receives at least a measure of user endocrine function as inputs and produces an output representing a variance between actuarial life expectancy and a projected actual mortality date, where providing an output "representing" a variance means an output from which a variance can be calculated, including providing the actuarial life expectancy and projected actual mortality date as two output elements, providing the difference between the actuarial life expectancy and a projected actual mortality date, and/or providing a raw score, for instance as described above. For example, and without limitation, at least a server 104 may generate, using a supervised machine-learning process, an endocrinal age factor model 124 that receives at least a measure of user endocrine function as inputs and produces an output representing a variance between actuarial life expectancy and a projected actual mortality date. At least a server 104 may then determine the user endocrinal age factor using the at least an endocrinal measure and the endocrinal age factor model 124, by inputting the at least an endocrinal measure into the endocrinal age factor model 124, and receiving an output; output may be a raw score as described above, which at least a server 104 may multiply by a weight to obtain the endocrinal age factor.

With continued reference to FIG. 1, where endocrinal training set 120 correlates one or changes in measures of endocrinal function to variances between actuarial life expectancy and actual mortality dates, at least a server 104 may use the endocrinal training set 120 to generate an endocrinal age factor model 124, which may include any machine-learning model that receives one or more changes in endocrinal measures as inputs and produces an output representing a variance between actuarial life expectancy and a projected actual mortality date, where providing an output "representing" a variance means an output from which a variance can be calculated, including providing the actuarial life expectancy and projected actual mortality date as two output elements, providing the difference between the actuarial life expectancy and a projected actual mortality date, and/or providing a raw score, for instance as described above. For example, and without limitation, at least a server 104 may generate, using a supervised machine-learning process, an endocrinal age factor model 124 that receives one or more changes endocrinal measures as inputs and produces an output representing a variance between actuarial life expectancy and a projected actual mortality date. At least a server 104 may then determine the user endocrinal age factor using the at least an endocrinal measure and the endocrinal age factor model 124, by inputting a change in endocrinal measure determined using the at least an endocrinal measure into the endocrinal age factor model 124, and receiving an output; output may be a raw score as described above, which at least a server 104 may multiply by a weight to obtain the endocrinal age factor.

Still referring to FIG. 1, at least a server 104 may be configured to classify user to at least an endocrinal life phase as a function of the at least a measure of endocrinal function. As noted above, over a human lifespan, endocrinal measures may go up or down in characteristic ways, for instance as described above. At least a server 104 may divide a human lifespan into contiguous periods, described herein as "endocrinal life phases," into which data describing one or more users may be classified using one or more measures of endocrine function. This may be accomplished, without limitation, by generating a life phase classifier 128 using a supervised machine learning process. For instance, and without limitation, at least a server 104 may receive a life phase training set 132 including a plurality of entries correlating one or more measures of endocrine function to chronological ages, and train, using a supervised machine-learning process, a classifier that takes at least a measure of endocrine function and outputs a classification to an endocrinal life phase, using the life phase training set 132. At least a server 104 may use life phase classifier 128 to determine an endocrinal life phase of user by providing at least a measure of endocrine function, as obtained from user blood sample as described above, as an input to life phase classifier 128, and receiving an endocrinal life phase as an input. Any set of training data described in this disclosure may be limited to a cohort sharing an endocrinal life phase with a user; this may be done by classifying each entry of any set of training data using life phase classifier 128, and assembling a training set containing only entries classified to endocrinal life phases matching an endocrinal life phase of user as described above. In an embodiment, this may enable use of any machine-learning process as described herein with training data representing a cohort of persons sharing an endocrinal life phase with user; more accurate machine-learning results may be produced using training data so limited.

With continued reference to FIG. 1, at least a server 104 is designed and configured to record a user genetic sample including a measure of user telomer length, where "recording" a user genetic sample may include receiving data describing a user genetic sample that has been extracted from a user. A "user genetic sample" as used herein is a sample including any sequence of nucleic acid identified in a user, including without limitation deoxyribonucleic acid (DNA) and/or ribonucleic acid (RNA). DNA may include chromosomal DNA, including without limitation sequences encoding particular genes as well as sequences of DNA disposed between or after gene sequences, including without limitation telomeres. Telomeres, as used in this description are caps (repetitive nucleotide sequences) at the end of linear chromosomes of a user. Telomeres are theorized to play a critical role in facilitating complete chromosome replication. Telomeres are characterized by noncoding tandem arrays of a "TTAGGG" DNA sequence that are located at the terminal ends of all vertebrate chromosomes, including those of humans. A G-rich single stranded 3-prime overhang is present at the end of human telomeres; this overhang, which may be important for telomere function folds back on itself forming a large loop structure called a telomere loop, or T-loop, that has a shape similar to that of a paper clip. A telomere may be stabilized by a six-protein complex, known as "shelterin," which may include telomeric repeat binding factor 1 and 2 (TRF1 and TRF2), protection of telomeres 1(POT1), TRF1 and TRF2 interacting nuclear protein 2 (TIN2), the human ortholog of the yeast repressor/activator protein 1 (Rap1), and TPP1. Telomere lengths have been observed to reduce over a series of cellular mitotic divisions, such that telomere length and/or changes in telomere length appear to correlate with processes of cellular aging and senescence. It is therefore hypothesized that telomere length and/or changes thereto may be useful to predict life expectancy of a person; however, precise predictions have hitherto eluded researchers. A genetic sample may include mRNA, tRNA, or any other RNA sequence or strand.

Still referring to FIG. 1, extraction of a genetic sample from a user may include collection of a physically extracted sample from a user, including without limitation a tissue sample, a buccal swab, a fluid sample, a biopsy, or the like; in an embodiment, a blood sample used for extraction of at least a measure of user endocrine function as described above may be further processed to extract a genetic sample. Extraction of genetic samples may be performed using any suitable physical process, including separation of nucleic acid from other tissue and/or fluid elements using, without limitation, a centrifuge. Extraction may include any form of restriction or division of a DNA and/or RNA sequence into sub-sequences, including without limitation using restriction enzymes. Extraction of genetic samples may include one or more variations of polymerase chain reaction "PCR" processes, whereby a particular strand of nucleic acid is replicated or "amplified" in a solution of nucleic acid by repeatedly exposing the solution to stimulus, such as heat, that breaks base-pair bonds, and then removing the stimulus to allow base-pair bonds to reform; as a result, a strand or sequence of nucleic acid will bond to free-floating molecules of nucleic acid, forming an inverse copy of itself, which will be separated from the strand or sequence during stimulus, and subsequently each of the strand and the inverse copy will bond to further free-floating molecules. As the above-described process is repeated, the number of copies of the strand or sequence increases exponentially. Extraction may include any suitable process to measure sequence lengths, match sequences, or the like, including without limitation electrophoresis.

Still referring to FIG. 1, methods to identify telomere length may include any suitable method for measuring and/or estimating telomere length, which may be assessed as any suitable statistical aggregation of telomere length, including without limitation arithmetic and/or geometric means of measured telomere length. Methods for measurement of telomere length may include, without limitation, quantitative PCR (qPCR) DNA measurement methods, TRF DNA measurement methods, MMqPCR DNA measurement methods, aTLqPCR DNA measurement methods, STELA DNA measurement methods, Q-FISH Metaphase chromosome measurements, Q-FISH Interphase nuclei (telomere) measurements, PRINS Metaphase chromosomes measurements, PRINS Interphase nuclei (telomere) measurements, Flow-FISH interphase nuclei measurements, HT Q-FISH interphase nuclei measurements, or any other suitable technique that may occur to persons skilled in the art upon reviewing the entirety of this disclosure. Measure of telomere length may expressed in units of length; alternatively or additionally, telomere length may be expressed as a proportion or percentage of a previously measured telomere length. In other words, a measure of telomere length may include a change in telomere length as measured, for instance, in a previous iteration of methods as disclosed herein; a change in telomere length may be recorded as an absolute change, a relative change, a percentage, or in any other suitable form that may occur to persons skilled in the art upon reviewing the entirety of this disclosure.

With continued reference to FIG. 1, at least a server 104 may be designed and configured to determine a user telomeric age factor using the user telomere length. A "user telomeric age factor," as used in this disclosure, is a factor that may be multiplied by a user's chronological age to reflect an effect that telomeric length and/or a change in telomere length has on the user's effective age. Calculation may include prediction of a variance from actuarial life expectancy for a given person, as defined above, as determined based on telomeric length and/or variation in telomere length. A difference between these two values may be added to a user chronological age and then divided by the user chronological age to calculate a "raw" factor, for instance as described above; this may then be multiplied by a weight to determine the telomeric age factor, where as above the weight may be calculated to offset relatedness between telomere length and/or change in telomere length and other elements used to calculate age factors as described herein, such as endocrinal age factors. At least a server 104 may determine telomeric age factor by retrieving telomeric age factor from expert database 116. For instance, and without limitation, one or more experts may enter data in expert database 116 indicative of an effect on user life expectancy; such data may, for instance, be entered as described in further detail below.

Continuing to refer to FIG. 1, and as a non-limiting illustrative example, at least a server 104 may determine telomeric age factor by receiving a telomeric training set 136 correlating telomere length and/or change in telomere length to variances between actuarial life expectancy data, defined as above, and actual mortality dates defined as above. A "variance between actuarial life expectancy datum and actual mortality date" may include any variance between actuarial life expectancy datum and actual mortality date as described above. "Correlation" in telomeric training set 136 may include any relation established therein linking one datum to another, including inclusion together in a data element, row, column, cell, or the like, and/or by giving each a common indicator and/or label indicative of their correlation in data used to create and/or compile training data. Correlation of telomere length and/or change in telomere length to variances between actuarial life expectancy data and actual mortality dates may be accomplished by correlating, to a calculated variance, to a factor based on the calculated variance, which may include a user telomeric age factor or raw factor as described above; alternatively or additionally, such correlation may indicate correlation to actuarial life expectancy datum and/or a dataset suitable for looking up actuarial life expectancy, and to actual mortality date, or any other set of data from which such a variance may be deduced. In other words, and by way of illustration only, an actual mortality date per se may not be in a training set entry; instead it might be a difference between actuarial and actual life expectancies, a life expectancy plus chronological age (from which variance may be calculated), or the like. Telomeric training set 136 may include a plurality of entries, each entry correlating a measure of telomere length and/or a change in telomere length to a variance between actuarial life expectancy data and actual mortality date of a person.

Still referring to FIG. 1, at least a server 104 may perform one or more processes to modify and/or format training data to produce telomeric training set 136. At least a server 104 may, without limitation, modify entries in training data to contain consistent forms of a variance, for instance so that a regression process or other supervised machine-learning process may operate without converting data to particular forms during operation; alternatively, supervised machine-learning process may perform standardization calculations during operation. Other modifications may include receiving a training set correlating one or more other biomarkers to variances between actuarial life expectancy data and actual mortality dates, where variances, correlations, and entries may be implemented as described above; for instance, training data relating telomere length and/or changes in telomere length to variances between actuarial life expectancy data and actual mortality dates may be unavailable, but a training set relating one or more additional biomarkers to variances between actuarial life expectancy data and actual mortality dates may be received. At least a server 104 may use one or more additional machine learning processes to create telomeric training set 136 relating telomere length and/or changes in telomere length to variances between actuarial life expectancy data and actual mortality dates by modifying training data relating one or more additional biomarkers to variances between actuarial life expectancy data and actual mortality dates. For instance, and without limitation, at least as server may perform an unsupervised machine learning process on training data correlating telomere length and/or changes in telomere length with additional biomarkers, which may be any biomarkers; unsupervised machine learning may be used to cluster telomere length and/or changes in telomere length with one or more other biomarkers, for instance to identify one or more additional biomarkers that are highly correlated with telomere length and/or changes in telomere length. At least a server 104 may then modify the training data to create telomeric training set 136 by replacing one or more additional biomarkers in each entry the training data with a telomeric length and/or a change in telomere length that is correlated therewith by the unsupervised machine learning set. In an embodiment, this approach may make it possible to draw upon training data relating one or more biomarkers to mortality to measures of telomere length and/or changes in telomere length, as data describing actual dates of death may require data collection over a number of years, whereas data relating an additional biomarker to at least a measure of telomere length and/or changes in telomere length may be collected rapidly. At least a server 104 may alternatively or additionally limit telomeric training set 136 to a cohort of entries that are classified, by life phase classifier 128, to an endocrinal file phase to which life phase classifier 128 has classified user as described above.

With continued reference to FIG. 1, where telomeric training set 136 correlates telomere length to variances between actuarial life expectancy and actual mortality dates, at least a server 104 may use the telomeric training set 136 to generate a telomeric age factor model 140, which may include any machine-learning model that receives telomere length as inputs and produces an output representing a variance between actuarial life expectancy and a projected actual mortality date, where providing an output "representing" a variance means an output from which a variance can be calculated, including providing the actuarial life expectancy and projected actual mortality date as two output elements, providing the difference between the actuarial life expectancy and a projected actual mortality date, and/or providing a raw score, for instance as described above. For example, and without limitation, at least a server 104 may generate, using a supervised machine-learning process, a telomeric age factor model 140 that receives telomere length as input and produces an output representing a variance between actuarial life expectancy and a projected actual mortality date. At least a server 104 may then determine the user telomeric age factor using measure of telomere length and the telomeric age factor model 140, by inputting the measure of telomere length into the telomeric age factor model 140, and receiving an output; output may be a raw score as described above, which at least a server 104 may multiply by a weight to obtain the telomeric age factor.

With continued reference to FIG. 1, where telomeric training set 136 correlates one or changes in telomere length to variances between actuarial life expectancy and actual mortality dates, at least a server 104 may use the telomeric training set 136 to generate a telomeric age factor model 140, which may include any machine-learning model that receives a change in telomere length as input and produces an output representing a variance between actuarial life expectancy and a projected actual mortality date, where providing an output "representing" a variance means an output from which a variance can be calculated, including providing the actuarial life expectancy and projected actual mortality date as two output elements, providing the difference between the actuarial life expectancy and a projected actual mortality date, and/or providing a raw score, for instance as described above. For example, and without limitation, at least a server 104 may generate, using a supervised machine-learning process, a telomeric age factor model 140 that receives a change in telomere length input and produces an output representing a variance between actuarial life expectancy and a projected actual mortality date. At least a server 104 may then determine the user telomeric age factor using change in user telomere length and the telomeric age factor model 140, by inputting a change in telomeric length determined using the measure of user telomere length into the endocrinal age factor model 124, and receiving an output; output may be a raw score as described above, which at least a server 104 may multiply by a weight to obtain the user telomeric age factor.

Still referring to FIG. 1, at least a server 104 is configured to provide a user negative habit factor. A "user negative habit factor," as used in this disclosure, is a factor that may be multiplied by a user's chronological age to reflect an effect that a habit the user is engaged in has on the user's effective age. A habit a user is engaged in may be a nutritional habit, such as a daily consumption of sugar, fat, fiber, protein, or the like. A habit a user is engaged in may include an exercise habit, which may be measured in terms of a duration per day, week, or the like of cardiovascular exercise, resistance training exercise, or other exercise category, a number of steps per week taken, resting and/or total calorie consumption numbers, or the like. A habit a user is engaged in may include a substance abuse habit, including some measure of a dosage per period of time consumed of a harmful and/or addictive substance such as an opiate, alcohol, tobacco, stimulants such as cocaine, methamphetamine or the like, hallucinogens, narcotics, or other mood-altering chemicals. A habit a user is engaged in may include a sleep habit, including a number of hours per night a user sleeps, a number of nights a user goes with less than a recommended amount of sleep, or the like.

Calculation of a user negative habit factor may include prediction of a variance from actuarial life expectancy for a given person, where a variance is a difference between an actuarial life expectancy for that person and a projected number of years until death as determined based on the habit. A difference between these two values may be added to a user chronological age and then divided by the user chronological age to calculate a "raw" factor; this may then be multiplied by a weight to determine the user negative habit factor.

In an embodiment, providing a user negative habit factor may include identifying a user negative habit. User negative habit may be identified by a user entry; for instance, and without limitation, at least a server 104 may provide a user with a questionnaire in the form of one or more data fields requesting that the user identify activities in which the user engaged. Questions presented to a user may include a number of servings of alcohol a user consumes during a given period of time such as a day, a week or a year, a quantity of tobacco, drugs, or other substances that a user consumes during a given period of time, a number of hours a user sleeps in a night, or the like. A user may respond to such questions by selecting options corresponding to particular ranges of data, by setting sliders or other indicators of a quantity along a continuous range, by entering values in drop-down lists, and/or by typing in numbers or text. Another person may alternatively or additionally enter information concerning a user's negative habits.

Figure 2:
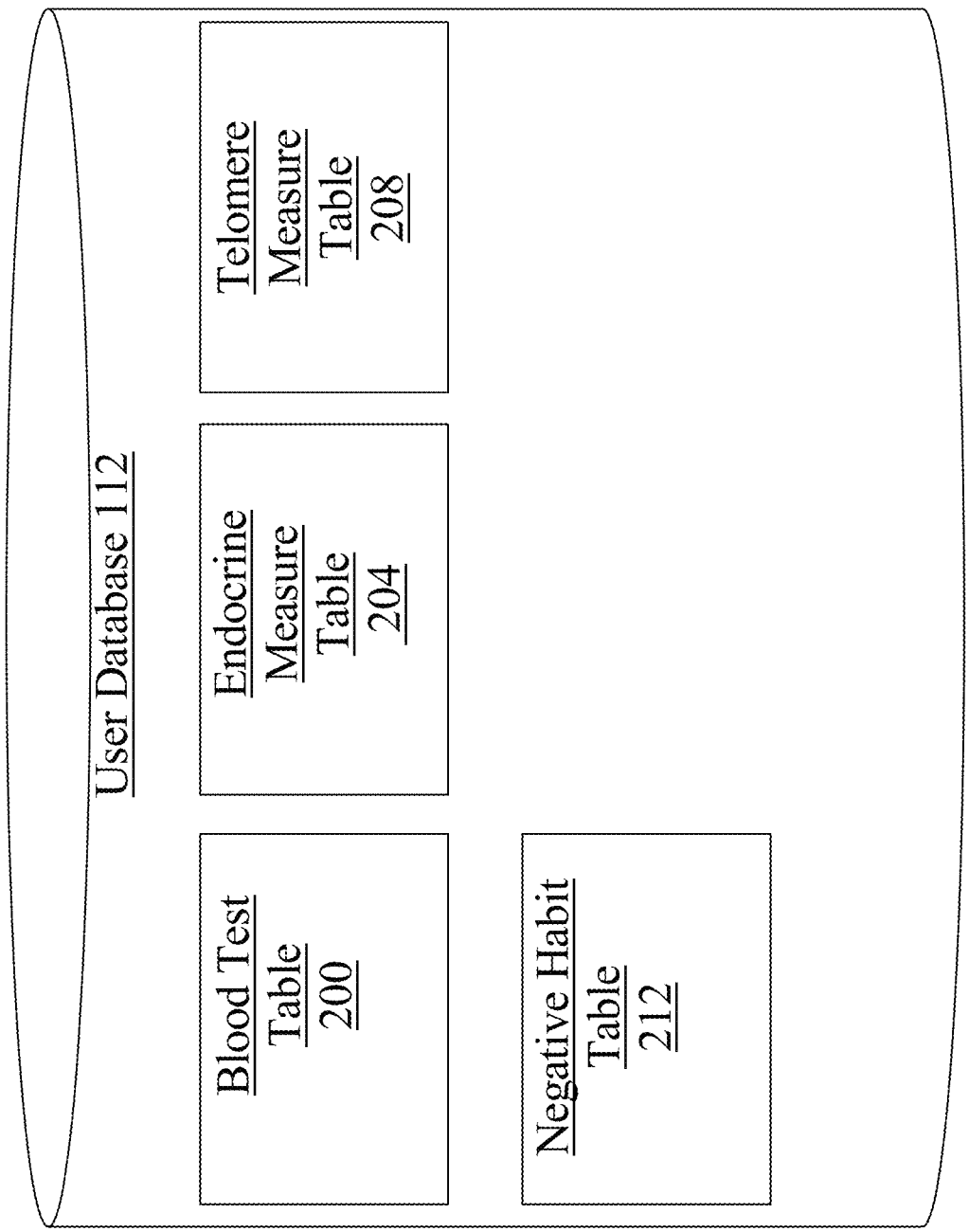
FIG. 2 is a block diagram illustrating an exemplary embodiment of a user database.

Alternatively or additionally, and still referring to FIG. 2, identifying a user negative habit may include receiving a training set correlating blood tests to negative habits, for instance by matching blood test results of individual who self-report particular negative habits. Identifying a user negative habit may include generating a user negative habit identifier model using a supervised machine-learning algorithm and the training set; negative habit identifier model may be generated, without limitation, using a classification algorithm, so that negative habit identifier may match a user blood test pattern to a most likely habit or a set of most likely habits of which user may partake. Identifying a user negative habit may include producing a negative habit output from the negative habit identifier model using the user blood test and identifying the user negative habit as a function of the negative habit output.

At least a system may provide the user negative habit factor based on the user negative habit. In an embodiment, this may be performed by consulting expert database 116; that is, one or more experts may provide data indicating a likely impact on life expectancy of a particular negative habit. For instance, an expert may provide an entry indicating that a lifelong smoking habit of one pack of cigarettes per day removes an average of 10 years of life expectancy; another expert may provide data indicative of a number of years of life expectancy lost to alcoholism, drug habits, consumption of too much saturated fat, or the like. Expert submissions may be based on information including without limitation studies or other academic materials.

Continuing to refer to FIG. 1, and as a non-limiting illustrative example, at least a server 104 may determine negative habit factor by receiving a negative habit training set 144 correlating one or more user negative habits and/or one or more changes in user negative habits to variances between actuarial life expectancy data and actual mortality dates. "Actuarial life expectancy data" and "actual mortality date" may be defined as described above. A "variance between actuarial life expectancy datum and actual mortality date" may include any such variance as described above. "Correlation" in a training data set may include any relation established therein linking one datum to another, including inclusion together in a data element, row, column, cell, or the like, and/or by giving each a common indicator and/or label indicative of their correlation in data used to create and/or compile training data. Correlation of one or more user negative habits and/or one or more changes in user negative habits to variances between actuarial life expectancy data and actual mortality dates may be accomplished by correlating to a calculated variance, to a factor based on the calculated variance, which may include a user negative habit factor; alternatively or additionally, such correlation may indicate correlation to actuarial life expectancy datum and/or a dataset suitable for looking up actuarial life expectancy, and to actual mortality date, or any other set of data from which such a variance may be deduced. In other words, and by way of illustration only, an actual mortality date per se may not be in a training set entry; instead it might be a difference between actuarial and actual life expectancies, a life expectancy plus chronological age (from which variance may be calculated), or the like. Negative habit training set 144 may include a plurality of entries, each entry correlating one or more user negative habits and/or one or more changes in user negative habits to a variance between actuarial life expectancy data and actual mortality date of a person.

Still referring to FIG. 1, at least a server 104 may perform one or more processes to modify and/or format training data to produce negative habit training set 144. At least a server 104 may, without limitation, modify entries in training data to contain consistent forms of a variance, for instance so that a regression process or other supervised machine-learning process may operate without converting data to particular forms during operation; alternatively, supervised machine-learning process may perform standardization calculations during operation. Other modifications may include receiving a training set correlating one or more other biomarkers to variances between actuarial life expectancy data and actual mortality dates, where variances, correlations, and entries may be implemented as described above; for instance, training data relating one or more user negative habits and/or changes in user negative habits to variances between actuarial life expectancy data and actual mortality dates may be unavailable, but a training set relating one or more additional biomarkers to variances between actuarial life expectancy data and actual mortality dates may be received. At least a server 104 may use one or more additional machine learning processes to create negative habit training set 144 relating one or more user negative habits and/or changes in user negative habits to variances between actuarial life expectancy data and actual mortality dates by modifying training data relating one or more additional biomarkers to variances between actuarial life expectancy data and actual mortality dates. For instance, and without limitation, at least as server may perform an unsupervised machine learning process on training data correlating one or more user negative habits and/or changes in user negative habits with additional biomarkers, which may be any biomarkers; unsupervised machine learning may be used to cluster one or more user negative habits and/or changes in user negative habits with one or more other biomarkers, for instance to identify one or more additional biomarkers that are highly correlated with one or more user negative habits and/or changes in user negative habits. At least a server 104 may then modify the training data to create negative habit training set 144 by replacing one or more additional biomarkers in each entry of the training data with a one or more user negative habits and/or changes in user negative habits that is correlated therewith by the unsupervised machine learning set. In an embodiment, this approach may make it possible to draw upon training data relating one or more biomarkers to mortality to measures of one or more user negative habits and/or changes in user negative habits, as data describing actual dates of death may require data collection over a number of years, whereas data relating an additional biomarker to one or more user negative habits and/or changes in user negative habits may be collected rapidly. Any negative habit training set 144 may be limited to a cohort of persons and/or data sets, such as limiting to entries corresponding to persons classified to an endocrinal life phase to which user has been classified as described above.

With continued reference to FIG. 1, where negative habit training set 144 correlates user negative habits to variances between actuarial life expectancy and actual mortality dates, at least a server 104 may use the negative training set to generate an negative habit factor model 148, which may include any machine-learning model that receives one or more user negative habits as inputs and produces an output representing a variance between actuarial life expectancy and a projected actual mortality date, where providing an output "representing" a variance means an output from which a variance can be calculated, including providing the actuarial life expectancy and projected actual mortality date as two output elements, providing the difference between the actuarial life expectancy and a projected actual mortality date, and/or providing a raw score, for instance as described above. For example, and without limitation, at least a server 104 may generate, using a supervised machine-learning process, a negative habit factor model 148 that receives one or more user negative habits as inputs and produces an output representing a variance between actuarial life expectancy and a projected actual mortality date. At least a server 104 may then determine the user negative habit factor using an identified at least a user negative habit and the negative habit factor model 148, by inputting the one or more user negative habits into the negative habit factor model 148, and receiving an output; output may be a raw score as described above, which at least a server 104 may multiply by a weight to obtain the user negative habit factor.

With continued reference to FIG. 1, where negative habit training set 144 correlates one or changes in user negative habits to variances between actuarial life expectancy and actual mortality dates, at least a server 104 may use the negative habit training set 144 to generate a negative habit factor model 148, which may include any machine-learning model that receives a change in one or more user negative habits input and produces an output representing a variance between actuarial life expectancy and a projected actual mortality date, where providing an output "representing" a variance means an output from which a variance can be calculated, including providing the actuarial life expectancy and projected actual mortality date as two output elements, providing the difference between the actuarial life expectancy and a projected actual mortality date, and/or providing a raw score, for instance as described above. For example, and without limitation, at least a server 104 may generate, using a supervised machine-learning process, a negative habit factor model 148 that receives a change in one or more user negative habits and produces an output representing a variance between actuarial life expectancy and a projected actual mortality date. At least a server 104 may then determine the user negative habit factor using change in one or more user negative habits and the telomeric age factor model 140, by inputting a change in user negative habit determined negative habit factor model 148, and receiving an output; output may be a raw score as described above, which at least a server 104 may multiply by a weight to obtain the user negative habit factor.

In an embodiment, and still referring to FIG. 1, at least a server 104 may be provided with one or more weights to multiply with raw factors to obtain user endocrinal age factor, user telomeric age factor and/or user negative habit factor. Such weights may be provided by experts; for instance, at least a server 104 may recover weights from expert database 116. Alternatively or additionally at least a server 104 may generate weights using unsupervised machine-learning procedures. For instance, and without limitation, at least a server 104 may receive a factor dependency training set 152 having entries correlating at least a measure of endocrine function, telomere length, and negative habits. An unsupervised machine learning process may use factor dependency training set 152 to determine a set of outputs indicating a degree of interrelatedness between at least a measure of endocrine function, telomere length, and negative habits; this may be used to create a factor dependence model, which may receive, for instance, an input set representing at least a measure of endocrine function, telomere length, and negative habit data for a user and outputting weights to be multiplied by each raw factor so that each of user telomeric age factor, user endocrinal age factor and user negative habit factor is reduced in proportion to its likely dependency on the other factors and/or their dependency on it. This may prevent at least a server 104 from overestimating the combined impact of all three factors on life expectancy, by accounting for the degree to which all three factors may depend upon each other.

Referring now to FIG. 2, an exemplary embodiment of a user database 112 is illustrated. One or more database tables in user database 112 may include, as a non-limiting example, a blood test table 200, which may record data received by at least a server 104 regarding a user blood test as described above. One or more database tables in user database 112 may include, as a non-limiting example, an endocrine measure table 204, which may record data received by at least a server 104 regarding at least a measure of user endocrine function as described above. One or more database tables in user database 112 may include, as a non-limiting example, a telomere measure table 208, which may record data received by at least a server 104 regarding at least a measure of telomere length as described above. One or more database tables in user database 112 may include, as a non-limiting example, negative habit table 212, which may record data received by at least a server 104 regarding a user negative habit as described above.

Figure 3:
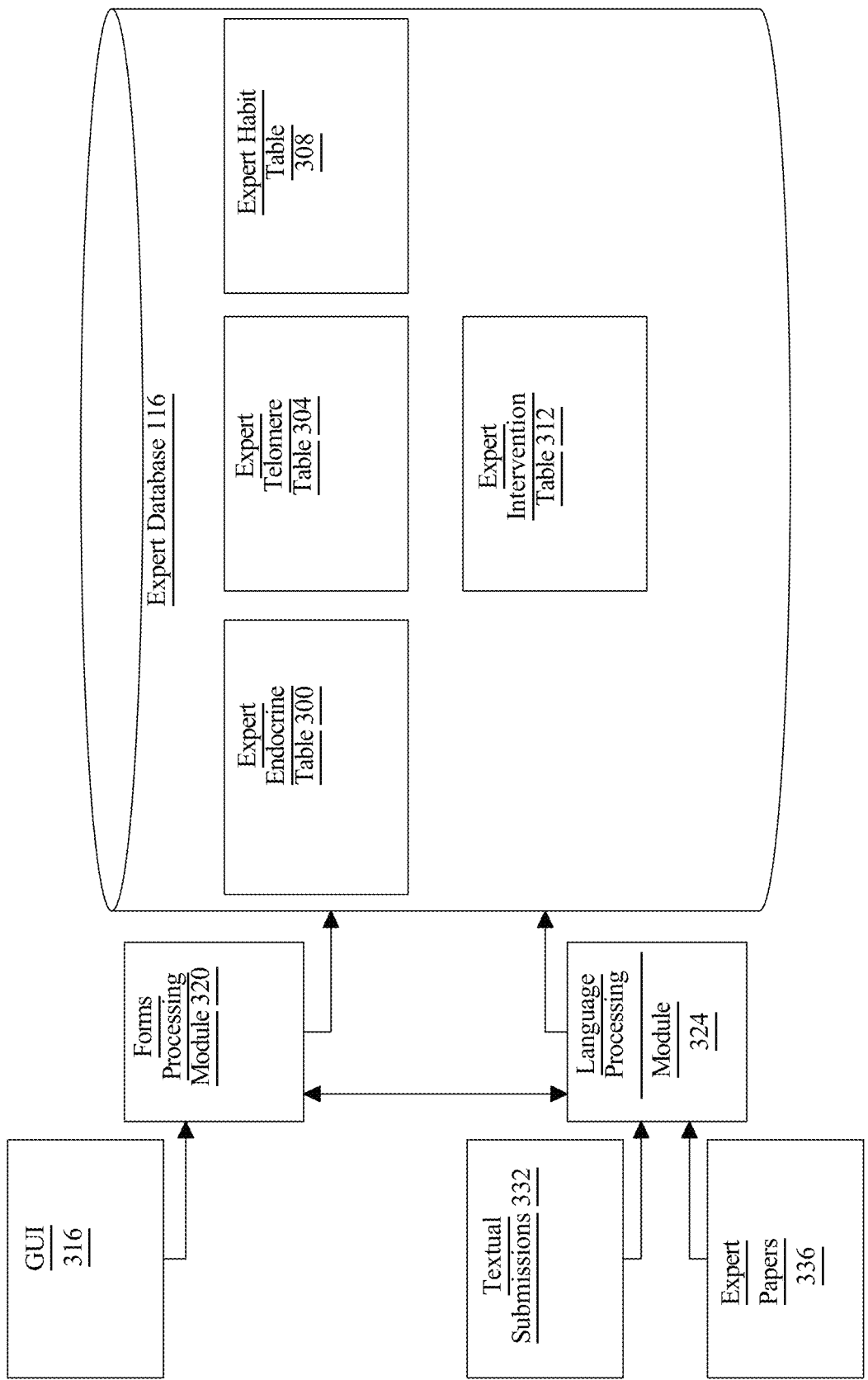
FIG. 3 is a block diagram illustrating an exemplary embodiment of an expert database.

Referring now to FIG. 3, an exemplary embodiment of an expert database 116 is illustrated. Expert database 116 may, as a non-limiting example, organize data stored in the expert database 116 according to one or more database tables. One or more database tables may be linked to one another by, for instance, common column values. For instance, a common column between two tables of expert database 116 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 3, one or more database tables in expert database 116 may include, as a non-limiting example, an expert endocrine table 300. Expert endocrine table 300 may include any information provided by one or more experts regarding at least a measure of user endocrine function, user endocrinal age factor, and/or other expert data regarding endocrinal information as described in this disclosure. One or more database tables in expert database 116 may include, as a non-limiting example, an expert telomere table 304. Expert telomere table 304 may include any information provided by one or more experts regarding user telomer length, user telomeric age factor, and/or other expert data regarding telomere related information as described in this disclosure. One or more database tables in expert database 116 may include, as a non-limiting example, an expert negative habit table 304. Expert negative habit table 304 may include any information provided by one or more experts regarding user negative habits length, user negative habit factor, and/or other expert data regarding negative habit related information as described in this disclosure. One or more database tables in expert database 116 may include, as a non-limiting example, an expert intervention table 308. Expert intervention table 308 may include any information provided by one or more experts regarding interventions, intervention elements, and/or vectors associated therewith, as described in further detail below.

In an embodiment, and still referring to FIG. 3, a forms processing module 312 may sort data entered in a submission via a graphical user interface 316 receiving expert submissions by, for instance, sorting data from entries in the graphical user interface 316 to related categories of data; for instance, data entered in an entry relating in the graphical user interface 316 to endocrinal data may be sorted into variables and/or data structures for endocrinal data, which may be provided to expert endocrinal table 300, while data entered in an entry relating to telomere length may be sorted into variables and/or data structures for the storage of, telomere length data, such as expert telomeric table 304. Where data is chosen by an expert from pre-selected entries such as drop-down lists, data may be stored directly; where data is entered in textual form, a language processing module may be used to map data to an appropriate existing label, for instance using a vector similarity test or other synonym-sensitive language processing test to map data to existing labels and/or categories. Similarly, data from an expert textual submissions 320, such as accomplished by filling out a paper or PDF form and/or submitting narrative information, may likewise be processed using language processing module.

Still referring to FIG. 3, a language processing module 324 may include any hardware and/or software module. Language processing module 324 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, language processing module 324 may compare extracted words to categories of data to be analyzed; such data for comparison may be entered on at least a server 104 as described above using expert data inputs or the like. In an embodiment, one or more categories may be enumerated, to find total count of mentions in such documents. Alternatively or additionally, language processing module 324 may operate to produce a language processing model. Language processing model may include a program automatically generated by at least a server and/or language processing module 324 to produce associations between one or more words extracted from at least a document and detect associations, including without limitation mathematical associations, between such words, and/or associations between such words and other elements of data analyzed, processed and/or stored by system 100. Associations between language elements, may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of physiological data, a given relationship of such categories to prognostic labels, and/or a given category of prognostic labels. As a further example, statistical correlations and/or mathematical associations may include probabilistic formulas or relationships indicating a positive and/or negative association between at least an extracted word and/or a given category of data; positive or negative indication may include an indication that a given document is or is not indicating a category of data.

Still referring to FIG. 3, language processing module 324 and/or at least a server 104 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated.

In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted word category of physiological data, a given relationship of such categories to prognostic labels, and/or a given category of prognostic labels. There may be a finite number of category of physiological data, a given relationship of such categories to prognostic labels, and/or a given category of prognostic labels to which an extracted word may pertain; an HMM inference algorithm, such as the forward-backward algorithm or the Viterbi algorithm, may be used to estimate the most likely discrete state given a word or sequence of words. Language processing module 324 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 3, language processing module 324 may use a corpus of documents to generate associations between language elements in a language processing module 324, and at least a server 104 may then use such associations to analyze words extracted from one or more documents. Documents may be entered into classification device 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, classification device 104 may automatically obtain the document using such an identifier, for instance by submitting a request to a database or compendium of documents such as JSTOR as provided by Ithaka Harbors, Inc. of New York.

Data may be extracted from expert papers 328, which may include without limitation publications in medical and/or scientific journals, by language processing module 324 via any suitable process as described herein. Persons skilled in the art, upon reviewing the entirety of this disclosure, will be aware of various additional methods whereby novel terms may be separated from already-classified terms and/or synonyms therefore, as consistent with this disclosure.

Referring again to FIG. 1, at least a server 104 may be configured to calculate at least a user effective age. Calculating at least a user effective age includes multiplying a user chronological age by the user telomeric age factor, the user endocrinal age factor, and the user negative habit factor;

Still referring to FIG. 1, derive a user health quality vector 156; at user health quality vector 156 may be a data structure that represents a quantitative measure of a degree of importance a user places on each of a plurality of user goals, including decrease in user effective age, or equivalently increase in life expectancy, and at least one other distinct priority. A user health quality vector 156, as defined in this disclosure, is n n-tuple of values, where n is at least two values, as described in further detail below. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\Sigma_{i=0}^{n}a_i^2}$, where a is attribute number i of the vector. Scaling and/or normalization may function to make vector comparison independent of absolute quantities of attributes, while preserving any dependency on similarity of attributes; this may, for instance be advantageous where each vector represents a weighing of user priorities, and/or is to be compared to such a weighing of user priorities.

Continuing to refer to FIG. 1, user health quality vector 156 includes a plurality of health vector entries, which are attributes of user health quality vector 156 as described above. Plurality of health vector entries includes an effective age reduction value indicating a degree of importance of effective age reduction. Plurality of health vector entries includes at least a life quality objective value indicating a numerical measure of a user life quality priority. At least a life quality objective may include, for instance, an attribute indicating a degree of importance to user of cost of an action that may be taken to improve life expectancy, such as an intervention and/or intervention element as described in further detail below. At least a life quality objective may include an attribute indicating a degree of importance to user of a negative habit. At least a life quality objective may include an attribute indicating a degree of importance to user of schedule commitment, where, for instance, a larger number may indicate a greater reluctance to schedule regular sessions, exercise programs, bedtimes, or the like. At least a life quality objective may include an attribute indicating a degree of importance to user of time commitment, which may include a numerical measure of a degree to which user is bothered by having to set aside a given amount of time in a week, day, month and/or year. At least a life quality objective may include an attribute indicating a degree of importance to user of a change in diet. Persons skilled in the art, upon reviewing the entirety of this disclosure, will be aware of various additional attributes that may be used for at least a life quality objective in user health quality vector 156.

Referring again to FIG. 1, at least a server 104 may derive user quality health vector by receiving at least a user input. For instance, a graphical user interface may display at user device options to rate one or more priorities absolutely and/or relatively to each other, for instance by providing a numerical rating scale with radio buttons and/or drop-down lists, sliders where a user may set relative importance along a continuum for each user health quality vector 156 attribute, and/or textual entry fields wherein a user may enter numbers reflecting user's personal degree of importance for each field.

Alternatively or additionally, and still referring to FIG. 1, deriving the user health quality vector 156 may include generating a default vector; a default vector may contain default values that represent a "first guess" by system 100 for what user's relative priorities are likely to be. Default vector may be stored in and/or retrieved from expert database 116, which may be populated based on an expert determination of likely priorities. Alternatively, a person acquainted with user may enter, in a display as described above, what that person believes user's priorities are likely to be; multiple such entries may be aggregated, averaged, or the like. In an embodiment, at least a server 104 may use a machine-learning process to generate a default vector; this may be performed by predicting a user's likely priorities and/or preferences based on previously determined priorities and/or preferences of another person. For instance, generating a default vector may include receiving a default vector training set correlating a cohort of individual information to individual health quality vectors. Default vector training set may include a plurality of entries, each entry corresponding to a different person; entries may be anonymized to preserve individual privacy. Each entry of plurality of entries may include a set of personal data, pertaining to a person represented by the entry, which may include any information suitable for inclusion in user database 112 as described above, including user preferences, habits, health information including without limitation blood test, endocrinal, genetic, and/or telomeric data, user negative habit data, user demographic data, and the like. Each entry may also include a user health quality vector 156, which may include any element and/or elements suitable for inclusion in user health quality vector 156 as described above. In an embodiment, at least a server 104 may classify each entry to an endocrinal life phase, for instance and without limitation using life phase classifier 128. Endocrinal life phase may be added to each entry and used as a further matching criterion; alternatively or additionally, default vector training set may be limited to a cohort of entries having endocrinal life phases matching an endocrinal life phase of user, which may be determined as described above.

Still referring to FIG. 1, at least a server 104 may generating a set of user data regarding the user; set of user data may be generated to match categories of data in entries in default vector training set. In an embodiment set of user data may be generated by querying user database 112. Alternatively or additionally, one or more elements of set of user data may be obtained by prompting user to enter the one or more elements at a user device and receiving the one or more elements in response to the prompting; one or more elements may be obtained, alternatively or additionally, by prompting another person, for instance at or via an additional client device, to provide the one or more elements of data, and receiving the one or more elements in response. The above-described methods may be combined; for instance, at least a server 104 may query user database 112 to obtain some elements of user data, determine that one or more elements matching categories in default vector database are missing, and prompt user and/or another person to provide such elements. Persons skilled in the art, upon reviewing the entirety of this disclosure, will be aware of various ways in which user data may be collected and/or generated consistently with this disclosure.

With continued reference to FIG. 1, at least a server 104 may derive default vector from training set as a function of set of user data, using any suitable machine learning algorithm. As a non-limiting example, at least a server 104 may derive default vector from training set using a lazy-learning process, which may be a K-nearest neighbors algorithm; K-nearest neighbors may return a single matching entry, or a plurality of matching entries. Where a plurality of matching entries are returned, at least a server 104 may derive default vector from plurality of matching entries by aggregating user health quality vector 156s of matching entries; aggregation may be performed using any suitable method for aggregation, including component-wise addition followed by normalization, component-wise calculation of arithmetic means, or the like. Persons skilled in the art, upon reviewing the entirety of this disclosure, will be aware of various ways in which multiple user health quality vector 156s may be combined to create a default vector.

Still referring to FIG. 1, deriving the user health quality vector 156 may additionally include displaying a default vector to the user. Default vector may be displayed to user via a user device. In an embodiment, display of default vector to user may be performed by populating data entry fields usable for user to enter values of user health vector with values taken from default vector. Such populated data entry fields may be displayed to user, indicating a first guess at user's likely preferences. At least a server 104 may receive a user command modifying the default vector; command may be received in the form of a modification and/or replacement by user of a value displayed in a user entry field. At least a server 104 may derive user health quality vector 156 using the default vector and the user command; for instance, and without limitation, system may adopt user modifications to default vector to produce a user health quality vector 156.

Still referring to FIG. 1, user health quality vector 156 may be stored in memory of at least a server 104, including without limitation in user database 112 as described above. User health quality vector 156 may be updated periodically; for instance a user may modify user health quality vector 156 via a user interface, for instance to change one or more relative priorities to match user health quality vector 156. User may enter a command to view user health quality vector 156, modify one or more parameters and/or attributes of user health quality vector 156, and cause at least a server 104 to store modified at least a user health quality vector 156.

With continued reference to FIG. 1, at least a server 104 is designed and configured to generate a plurality of interventions. An "intervention" is a set of actions, called "intervention elements," a user can take that, taken together, probably will reduce effective age, where probability is determined by a process as described herein for predicting that an intervention will reduce effective age. Each such intervention element may be stored in an intervention element database 160, which may be implemented in any manner suitable for implementation of user database 112 as described above.

Figure 4:
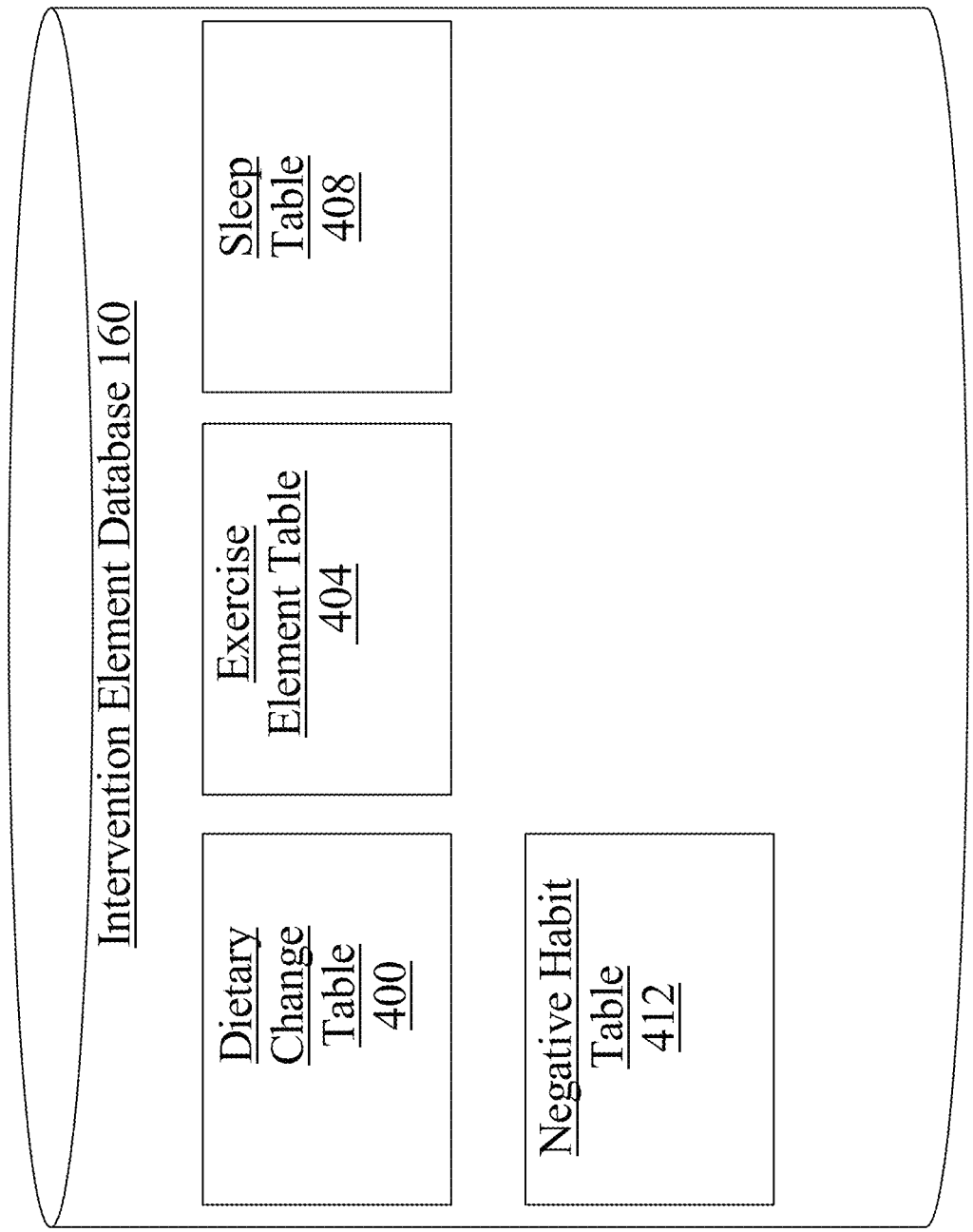
FIG. 4 is a block diagram illustrating an exemplary embodiment of an intervention element database.

Referring now to FIG. 4, an exemplary embodiment of intervention element database 160 is illustrated. Intervention element database 160 may include a dietary change table 400, which may contain, without limitation, intervention elements corresponding to dietary changes, such as without limitation a reduction in the daily consumption of a particular nutrient, an increase in the daily consumption of a particular nutrient, a decrease in the daily consumption of a given category of food, an increase in the daily consumption of a given category of food, or the like. For instance, and without limitation, an intervention element may include cessation of meat consumption, an addition of one serving of fruit per day, a halving of daily saturated fat intake as measured in calories and/or grams of saturated fat, or the like. Intervention elements pertaining to nutritional goals may list particular meals, meal plans, food elements, or the like, together with corresponding nutritional goals met by such meals, meal plans, and/or food elements. Intervention element database 160 may include an exercise element table 404, which may contain intervention elements that include one or more measurable exercise goals, such as a goal to take some target number of steps per day, a goal to burn a target number of calories per day, a goal to engage in a certain amount of cardiovascular exercise at a given intensity level, as represented for instance by a number on a discrete scale from 1 to 10, where 1 is a minimal intensity and 10 is a maximal intensity, a goal to engage in a certain amount of resistance training at a given intensity level, which may be similarly represented, a goal to spend a certain quantity of time per day stretching, or the like. Intervention elements pertaining to exercise goals may include particular forms of exercise, such as jogging, biking, weightlifting, or the like, which may list corresponding exercise goals that match the intervention elements. Intervention element database 160 may include, without limitation, a sleep table 408, which may record one or more intervention elements to sleep goals, such as a goal to sleep a certain number of hours per week or per day, to set a fixed bedtime, or the like. Intervention element table may include, without limitation, a negative habit table 412, which may record information elements relating to a cessation or reduction of a negative habit, such as tobacco consumption, alcohol consumption, gambling, drug use, or the like; such intervention elements may alternatively or additionally list particular programs and/or protocols for reduction in bad habits, such as 12-step programs or the like.

Referring again to FIG. 1, at least a server 104 may generate each intervention of plurality of interventions by combining intervention elements, which may be retrieved from intervention element database 160. Intervention elements for combinations may be selected according to intervention elements likely to improve a particular user's state of health; such elements may be identified, without limitation, using expert inputs; for instance expert inputs may link particular endocrinal levels and/or change in endocrinal levels to particular nutritional goals, exercise goals, sleep goals, or cessation of bad habits, which may in turn be used to retrieve particular intervention elements from intervention element database 160. As another non-limiting example, one or more expert inputs may identify reductions in bad habits that may improve user life expectancy, one or more programs that may aid in cessation of one or more bad habits, or the like. One or more expert inputs may propose one or more combinations of intervention elements that an expert may opine are especially useful, and/or that an expert may have viewed in the past as efficacious or convenient.

Still referring to FIG. 1, intervention element combinations may be selected using machine learning processes. For instance, an intervention training set including a plurality of entries may be received, each entry including a profile of a person having given endocrinal levels, telomere lengths, and/or negative habits, an intervention engaged in by that person, and effect of the intervention on a life expectancy of that person; intervention training set may be limited to cohorts of persons sharing an endocrinal life phase with user, persons sharing a chronological age with user, and/or persons sharing an effective age with user. A machine-learning process may identify persons having the greatest similarity to user, where similarity is matched according to endocrinal levels, telomere lengths, and/or negative habits, combined with a life-expectancy improvement goal from user health quality vector 156. A list of interventions may be selected using a K-nearest neighbors algorithm, a classifier, a lazy-learning algorithm, or a "best match" algorithm. Alternatively or additionally, an intervention or intervention component may be generated and/or selected by submitting any blood test data, genetic data, measure of endocrine function, telomere length or the like to a diagnostic engine configured to generate "ameliorative process labels," defined as labels describing one or more forms of actions that may tend to improve conditions and/or potential future conditions of a person, receiving, from the diagnostic engine, at least an ameliorative process label, and generating and/or selecting an intervention and/or intervention component as a function of the at least an ameliorative process label; such a diagnostic engine may be implemented, without limitation, as disclosed in U.S. Nonprovisional patent application Ser. No. 16/354,119, filed on Mar. 14, 2019, and entitled ARTIFICIAL INTELLIGENCE SYSTEMS AND METHODS FOR VIBRANT CONSTITUTIONAL GUIDANCE, the entirety of which is incorporated by reference herein.

With continued reference to FIG. 1, each intervention of the plurality of interventions includes an intervention vector including a plurality of intervention vector entries; intervention vector, in any given embodiment, may have entries corresponding to entries in user health quality vector 156. For instance, and without limitation, each intervention element may have an associated vector, which may be chosen as a subset of attributes of intervention element listed in a database, where each attribute indicates an effect each intervention element has on an attribute in user health quality vector 156; for example, a particular intervention element may have a large impact on life expectancy, represented by a large number in an attribute field associated with change to life expectancy, a low cost, represented by a small number in a field associated with cost, and require a large weekly time commitment, indicated by a large number in a field associated with weekly time commitment. Vectors associated with intervention elements may be stored in intervention element database 160 and linked to particular intervention elements; these vectors may, without limitation, be populated by expert inputs, aggregated user ratings, or the like. At least a server 104 may generate a vector of each intervention of plurality of interventions by combining intervention elements, for instance via component-wise addition; each intervention's vector may then be scaled and/or normalized as described above. As a result, each intervention vector entry may indicate a degree of relative impact on a factor represented by a health vector entry resulting from the intervention.

Still referring to FIG. 1, at least a server 104 is designed and configured to select an intervention from the plurality of interventions. In an embodiment, selecting the intervention further includes generating a loss function of the plurality of interventions and the user health quality vector 156, minimizing the loss function, and selecting an intervention from the plurality of interventions as a function of minimizing the loss function. A "loss function", as used herein is an expression of an output of which an optimization algorithm minimizes to generate an optimal result. As a non-limiting example, at least a server 104 may select an intervention having an associated vector that minimizes a measure of difference from user health quality vector 156; measure of difference may include, without limitation, a measure of geometric divergence between intervention vector and user health quality vector 156, such as without limitation cosine similarity, or may include any suitable error function measuring any degree of divergence and/or aggregation of degrees of divergence, between attributes of user heath quality vector and intervention vectors. Selection of different loss functions may result in identification of different interventions as generating minimal outputs. Alternatively or additionally, each of user health quality vector 156 and each intervention vector may be represented by a mathematical expression having the same form as mathematical expression; at least a server 104 may compare the former to the latter using an error function representing average difference between the two mathematical expressions. Error function may, as a non-limiting example, be calculated using the average difference between coefficients corresponding to each variable. An intervention having a mathematical expression minimizing the error function may be selected, as representing an optimal expression of relative importance of variables to a system or user. In an embodiment, error function and loss function calculations may be combined; for instance, a variable resulting in a minimal aggregate expression of error function and loss function, such as a simple addition, arithmetic mean, or the like of the error function with the loss function, may be selected, corresponding to an option that minimizes total variance from optimal variables while simultaneously minimizing a degree of variance from a set of priorities corresponding to variables. Coefficients of mathematical expression and/or loss function may be scaled and/or normalized; this may permit comparison and/or error function calculation to be performed without skewing by varied absolute quantities of numbers. Server may select a plurality of interventions to user; for instance, ranking may be maintained of interventions according to a degree to which they minimize loss function, and a number of highest-ranking interventions, such as the ten highest ranking interventions or the like, may be selected.

In an embodiment, and still referring to FIG. 1, at least a server 104 may be configured to present selected intervention and/or interventions to user; for instance, intervention vector each selected intervention may be presented. This may, in an embodiment, have the result that the user is able to see an impact on life expectancy of a given intervention, as well as its impact on one or more additional priorities that user has specified in user health quality vector 156. Server may additionally select an intervention maximizing impact on life expectancy, for instance by running loss function against a vector having all elements except life expectancy impact set to zero; this may be displayed as well to inform the user of a maximal possible impact on life expectancy. In an embodiment, at least a server 104 may receive user input modifying user health quality vector 156, for instance as described above; at least a server 104 may repeat above-described processes for selection of one or more interventions, including any cost-function process, and display selected interventions a second time.

Figure 5:
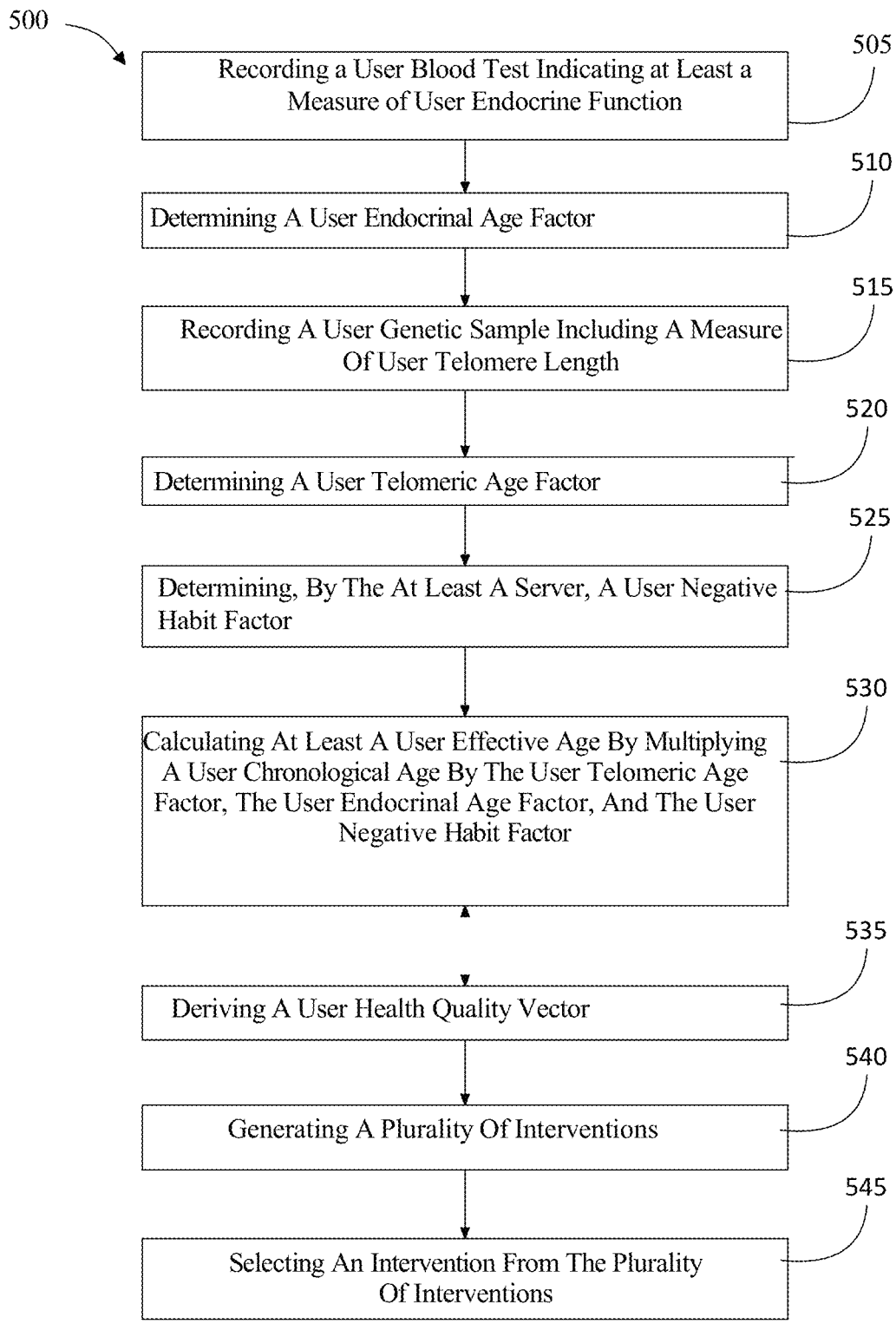
FIG. 5 is a flow diagram illustrating an exemplary embodiment of a method of selecting an intervention based on effective age.

Turning to FIG. 5, an exemplary embodiment of a method 500 of selecting an intervention based on effective age is illustrated. At step 505, at least a server 104 records a user blood test indicating at least a measure of user endocrine function; this may be implemented, without limitation, as described above in reference to FIGS. 1-4. At step 510, at least a server 104 determines a user endocrinal age factor using the at least a measure of user endocrine function; this may be implemented, without limitation, as described above in reference to FIGS. 1-4. For instance, and without limitation, determining user endocrinal age factor may include receiving training data correlating at least a measure of user endocrine function to variances between actuarial life expectancy datum and actual mortality dates, generating, using a supervised machine-learning process, an endocrinal age factor model 124 that receives at least a measure of user endocrine function as inputs and produces an output representing a variance between actuarial life expectancy and a projected actual mortality date, and determining the user endocrinal age factor using the at least a measure of endocrine function and the endocrinal age factor model 124. Alternatively or additionally, determining the user endocrinal age factor may include receiving training data correlating one or more changes in endocrinal measures to variances between actuarial life expectancy datum and actual mortality dates, generating, using a supervised machine-learning process, an endocrinal age factor model 124 that receives one or more changes in endocrinal measures as inputs and produces an output representing a variance between actuarial life expectancy and a projected actual mortality date, calculating at least a change in an endocrinal measure using the at least a measure of endocrine function, and determining the user endocrinal age factor using the at least a change in the endocrine measure and the endocrinal age factor model 124.

At step 515, and still referring to FIG. 5, at least a server 104 records a user genetic sample, where the user genetic sample includes a measure of user telomere length; this may be implemented, without limitation, as described above in reference to FIGS. 1-4. At step 520, at least a server 104 determines a user telomeric age factor using the user telomere length; this may be implemented, without limitation, as described above in reference to FIGS. 1-4. For instance, and without limitation, determining the user telomeric age factor may include receiving training data correlating telomere length to variances between actuarial life expectancy datum and actual mortality dates, generating, using a supervised machine-learning process, a telomeric age factor model 140 that receives telomeric length as input and produces an output representing a variance between actuarial life expectancy and a projected actual mortality date, and determining the user telomeric age factor using the user telomeric length and the telomeric age factor model 140. In an embodiment, at least a server 104 may identify, using a first unsupervised machine learning process, a correlation between at least a biomarker and telomere length, receive training data correlating the at last a biomarker to variances between actuarial life expectancy datum and actual mortality dates, and generate the training data correlating telomere length to variances between actuarial life expectancy datum and actual mortality dates using the training data correlating the at last a biomarker to variances between actuarial life expectancy datum and actual mortality dates and the correlation of between the at least a biomarker and telomere length.

With continued reference to FIG. 5, at step 525 at least a server 104 determine a user negative habit factor; this may be implemented, without limitation, as described above in reference to FIGS. 1-4. As a non-limiting example, determining a user negative habit factor may include identifying a user negative habit and providing the user negative habit factor based on the user negative habit. Identifying user negative habit may include receiving a training set correlating blood tests to negative habits, generating negative habit identifier model using a supervised machine-learning algorithm and the training set, producing a negative habit output from the negative habit identifier model using the user blood test, and identifying the user negative habit as a function of the negative habit output. Determining the user negative habit factor may include receiving training data correlating user negative habit to variances between actuarial life expectancy datum and actual mortality dates, generating, using a supervised machine-learning process, a user negative habit factor model 148 that receives negative habit ID as input and produces an output representing a variance between actuarial life expectancy and a projected actual mortality date, and determining the user negative habit age factor using the user telomeric length and the telomeric age factor model 140.

At step 530, and still referring to FIG. 5, at least a server 104 calculates at least a user effective age, wherein calculating the at least a user effective age further comprises multiplying a user chronological age by the user telomeric age factor, the user endocrinal age factor, and the user negative habit factor; this may be implemented, without limitation, as described above in reference to FIGS. 1-4.

At step 535, and continuing to refer to FIG. 5, at least a server 104 derives a user health quality vector 156, the user health quality vector 156 including a plurality of health vector entries including an effective age reduction value indicating a degree of importance of effective age reduction and at least a life quality objective value indicating a numerical measure of a user life quality priority; this may be implemented, without limitation, as described above in reference to FIGS. 1-4. For instance, and without limitation, deriving the user health quality vector 156 may include generating a default vector, displaying the default vector to the user, receiving a user command modifying the default vector, and deriving the user health quality vector 156 using the default vector and the user command. Generating default vector may include receiving a training set correlating a cohort of individual information to individual health quality vectors, generating a set of user data regarding the user, and deriving the default vector from the training set as a function of the set of user data using a K-nearest neighbors algorithm.

At step 540, the at least a server 104 generates a plurality of interventions, wherein each intervention of the plurality of interventions includes an intervention vector having a plurality of intervention vector entries, the plurality of intervention vector entries includes a vector entry corresponding to each health vector entry of the plurality of health vector entries, and each intervention vector entry indicates a degree of impact on a factor represented by a health vector entry; this may be implemented, without limitation, as described above in reference to FIGS. 1-4.

At step 545, at least a server 104 selecting, by the at least a server 104, an intervention from the plurality of interventions, where selecting the intervention includes generating a loss function of the plurality of interventions and the user health quality vector 156, minimizing the loss function, and selecting an intervention from the plurality of interventions as a function of minimizing the loss function; this may be implemented, without limitation, as described above in reference to FIGS. 1-4.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
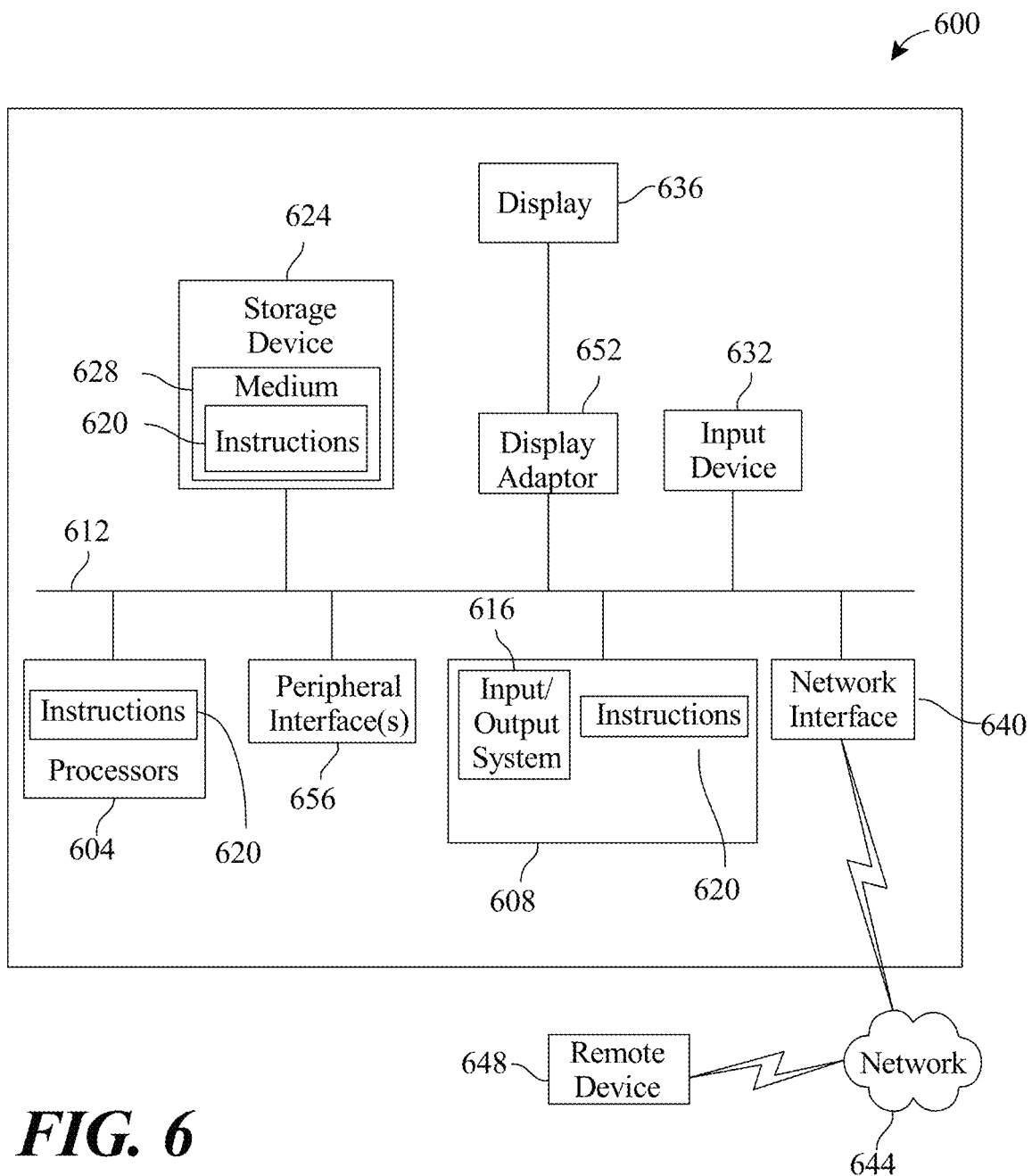
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Memory 608 may include various components (e.g., machine-readable media) including, but not limited to, a random-access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIRE-WIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for selecting an intervention based on effective age, the system comprising:
   at least a server, the at least a server designed and configured to:
   obtain user data from a user database, wherein the user data comprises data corresponding to user tests and a user chronological age, wherein at least a measure of user endocrine function is stored in the user database;
   project an actuarial life expectancy using the user chronological age;
   calculate a variance between the actuarial life expectancy and a projected actual mortality date, wherein calculating the variance comprises:
   receiving training data, wherein the training data correlates an aspect of the user data to the variance between the actuarial life expectancy and a projected actual mortality date;
   generating, using a supervised machine learning process, a machine learning model, wherein:
   the machine learning model comprises a life phase classifier trained by training data correlating the at least a measure of endocrine function to a user chronological age;
   the life phase classifier is configured to receive the at least a measure of endocrine function as input; and
   the life phase classifier is configured to output an endocrinal life phase;
   determining the variance between the actuarial life expectancy and a projected actual mortality date using the machine learning model;
   generate a plurality of interventions, wherein each intervention of the plurality of interventions comprises an intervention vector having a plurality of intervention vector entries, wherein each intervention vector entry indicates a degree of impact; and
   select an intervention from the plurality of interventions as a function of the degrees of impact and the variance between the actuarial life expectancy and a projected actual mortality date.

2. The system of claim 1, wherein the server is further designed and configured to classify the user into an endocrinal life phase, wherein classifying the user into the endocrinal life phase comprises determining the life phase of the user as a function the data corresponding to user tests.

3. The system of claim 1, wherein the server is further designed and configured to:

receive elements of user data from the user, wherein receiving the elements of user data from the user comprises:
  receiving the elements of user data, wherein the elements of user data of the user comprises data that is input by the user on a user device; and
  combining the elements of user data with the user data from the user database.

4. The system of claim 3, wherein the server is further designed and configured to recalculate the variance between the actuarial life expectancy and the projected actual mortality date, wherein recalculating the variance comprises repeating the step of calculating the variance between the actuarial life expectancy and the projected actual mortality date, using combined elements of user data and user data from the user database.

5. The system of claim 4, wherein the server is further designed and configured to reselect an intervention, wherein reselecting an intervention comprises repeating the step of selecting an intervention as a function of the recalculated variance between the actuarial life expectancy and the projected actual mortality date.

6. The system of claim 1, wherein the server is further designed and configured to:
receive elements of user data from another person, wherein receiving the elements of user data from the another person comprises:
  receiving the elements of user data, wherein the elements of user data of the user comprises data that is input by the another person on a client device; and
  combining the elements of user data with the user data from the user database.

7. The system of claim 1, wherein:
the server is further designed and configured to derive a user health quality vector, wherein the user health quality vector further comprises a plurality of health vector entries including:
  an effective age reduction value indicating a degree of importance of effective age reduction; and
  at least a life quality objective value indicating a numerical measure of a user life quality priority; and
selecting an intervention from the plurality of interventions is a function of one or more of the plurality of health vector entries of the user health quality vector.

8. The system of claim 7, wherein deriving the user health quality vector further comprises:
generating a default vector;
displaying the default vector to the user;
receiving a user command modifying the default vector; and
deriving the user health quality vector using the default vector and the user command.

9. The system of claim 8, wherein generating the default vector further comprises:
receiving a training set correlating a cohort of individual information to individual health quality vectors;
generating a set of user data regarding the user; and
deriving the default vector from the training set as a function of the set of user data using a K-nearest neighbors algorithm.

10. The system of claim 1, wherein the user data comprises blood test data.

11. A method for selecting an intervention based on effective age, the method comprising:
obtaining user data from a user database, wherein the user data comprises data corresponding to user tests and a user chronological age, wherein at least a measure of user endocrine function is stored in the user database;
projecting an actuarial life expectancy using the user chronological age;
calculating a variance between the actuarial life expectancy and a projected actual mortality date, wherein calculating the variance comprises:
  receiving training data, wherein the training data correlates an aspect of the user data to the variance between the actuarial life expectancy and a projected actual mortality date;
  generating, using a supervised machine learning process, a machine learning model, wherein:
    the machine learning model comprises a life phase classifier trained by training data correlating the at least a measure of endocrine function to a user chronological age;
    the life phase classifier is configured to receive the at least a measure of endocrine function as input; and
    the life phase classifier is configured to output an endocrinal life phase;
  determining the variance between the actuarial life expectancy and a projected actual mortality date using the machine learning model;
generating a plurality of interventions, wherein each intervention of the plurality of interventions comprises an intervention vector having a plurality of intervention vector entries, wherein each intervention vector entry indicates a degree of impact; and
selecting an intervention from the plurality of interventions as a function of the degrees of impact and the variance between the actuarial life expectancy and a projected actual mortality date.

12. The method of claim 11, further comprising classifying the user into an endocrinal life phase, wherein classifying the user into the endocrinal life phase comprises determining the life phase of the user as a function the data corresponding to user tests.

13. The method of claim 11, further comprising:
receiving elements of user data from the user, wherein receiving the elements of user data from the user comprises:
  receiving the elements of user data, wherein the elements of user data of the user comprises data that is input by the user on a user device; and
  combining the elements of user data with the user data from the user database.

14. The method of claim 13, further comprising recalculating the variance between the actuarial life expectancy and the projected actual mortality date, wherein recalculating the variance comprises repeating the step of calculating the variance between the actuarial life expectancy and the projected actual mortality date, using combined elements of user data and user data from the user database.

15. The method of claim 14, further comprising reselecting an intervention, wherein reselecting an intervention comprises repeating the step of selecting an intervention as a function of the recalculated variance between the actuarial life expectancy and the projected actual mortality date.

16. The method of claim 11, further comprising:
receiving elements of user data from another person, wherein receiving the elements of user data from the another person comprises:
  receiving the elements of user data, wherein the elements of user data of the user comprises data that is input by the another person on a client device; and combining the elements of user data with the user data from the user database.

17. The method of claim 11, further comprising:
deriving a user health quality vector, wherein the user health quality vector further comprises a plurality of health vector entries including:
   an effective age reduction value indicating a degree of importance of effective age reduction; and
   at least a life quality objective value indicating a numerical measure of a user life quality priority; and
wherein selecting an intervention from the plurality of interventions is a function of one or more of the plurality of health vector entries of the user health quality vector.

18. The method of claim 17, wherein deriving the user health quality vector further comprises:
generating a default vector;
displaying the default vector to the user;
receiving a user command modifying the default vector; and
deriving the user health quality vector using the default vector and the user command.

19. The method of claim 18, wherein generating the default vector further comprises:
receiving a training set correlating a cohort of individual information to individual health quality vectors;
generating a set of user data regarding the user; and
deriving the default vector from the training set as a function of the set of user data using a K-nearest neighbors algorithm.

20. The method of claim 11, wherein the user data comprises blood test data.

* * * * *